United States Patent
Vogt et al.

(10) Patent No.: US 9,592,319 B2
(45) Date of Patent: Mar. 14, 2017

(54) METHOD AND DEVICE FOR COATING OF A MEDICAL IMPLANT

(71) Applicant: Heraeus Medical GmbH, Wehrheim (DE)

(72) Inventors: Sebastian Vogt, Erfurt (DE); Hubert Buchner, Nuremberg (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 455 days.

(21) Appl. No.: 14/048,644

(22) Filed: Oct. 8, 2013

(65) Prior Publication Data

US 2014/0033970 A1    Feb. 6, 2014

Related U.S. Application Data

(62) Division of application No. 13/171,903, filed on Jun. 29, 2011, now Pat. No. 9,028,907.

(30) Foreign Application Priority Data

Jun. 29, 2010  (DE) .................. 10 2010 025 533

(51) Int. Cl.
| A61L 27/12 | (2006.01) |
| A61L 27/30 | (2006.01) |
| A61L 27/32 | (2006.01) |
| B05D 1/28  | (2006.01) |
| C23C 26/00 | (2006.01) |

(52) U.S. Cl.
CPC ............. *A61L 27/12* (2013.01); *A61L 27/306* (2013.01); *A61L 27/32* (2013.01); *A61L 2420/02* (2013.01); *B05D 1/28* (2013.01); *C23C 26/00* (2013.01)

(58) Field of Classification Search
None
See application file for complete search history.

(56) References Cited

U.S. PATENT DOCUMENTS

| 3,929,987 A | 12/1975 | Colodney et al. |
| 4,846,837 A | 7/1989 | Kurze et al. |
| 4,882,196 A | 11/1989 | Shimamune et al. |
| 5,251,468 A | 10/1993 | Lin et al. |
| 5,759,376 A | 6/1998 | Teller et al. |
| 6,069,295 A | 5/2000 | Leitao |
| 7,563,324 B1* | 7/2009 | Chen ............ B05C 1/022 118/264 |
| 2003/0031983 A1 | 2/2003 | Kotte et al. |
| 2003/0063944 A1* | 4/2003 | Leung ............ B05C 17/002 401/132 |
| 2006/0134160 A1 | 6/2006 | Troczynski et al. |
| 2006/0188541 A1 | 8/2006 | Richelsoph et al. |
| 2008/0003052 A1* | 1/2008 | Lee ............ A45D 34/041 401/209 |
| 2009/0304807 A1 | 12/2009 | Rhee et al. |

FOREIGN PATENT DOCUMENTS

| CN | 1874795 A | 12/2006 |
| CN | 101406711 A | 4/2009 |
| CN | 101485901 A | 7/2009 |
| DE | 10044062 A1 | 4/2002 |
| JP | 2005220336 A | 8/2005 |
| JP | 2008293904 A | 12/2008 |
| WO | 96/07438 A1 | 3/1996 |
| WO | 2004/024201 A2 | 3/2004 |
| WO | 2004/098436 A2 | 11/2004 |
| WO | 2007/147246 A1 | 12/2007 |
| WO | 2007147246 A1 | 12/2007 |
| WO | 2009/062671 A2 | 5/2009 |
| WO | 2009/147045 A1 | 12/2009 |

OTHER PUBLICATIONS

German Search Report for DE 11004744.6 dated Aug. 20, 2014.
English Translation of Chinese Office action for CN application No. 201110184543.X dated Dec. 4, 2013.
Chinese Office action for CN application No. 201110184543.X dated Dec. 4, 2013.
German Translation of JP Office Action for JP 2011-144133 dated Apr. 2, 2014.

* cited by examiner

*Primary Examiner* — Charles Capozzi
(74) *Attorney, Agent, or Firm* — Norris McLaughlin & Marcus P.A.

(57) ABSTRACT

Device for coating a medical implant, including a hollow body and a body arranged in the hollow body so as to be mobile therein and movable out of the hollow body at least in part; which body comprises at least one calcium salt with a Mohs hardness of no more than 5.5 on the surface thereof.

13 Claims, No Drawings

METHOD AND DEVICE FOR COATING OF A MEDICAL IMPLANT

This application is a division of U.S. patent application Ser. No. 13/171,903, filed Jun. 29, 2011, which claims priority of German Patent Application No. 102010025533.5, filed Jun. 29, 2010, now U.S. Pat. No. 9,028,907, issued May 12, 2015.

The invention relates to a method for coating of a medical implant, and relates in particular to a method for coating of a medical implant in a bone growth-promoting manner, as well as a device for implementation of said method.

Medical implants have been in use in medicine for a long time aiming to support or substitute for body functions. In particular defective joints of the body are replaced by articular implants with increasing success which often is associated with a substantial improvement in the quality of life of the respective patient.

Aside from cemented articular endoprostheses, non-cemented articular endoprostheses are also in use currently for replacement of hip, knee, and shoulder joints. Said non-cemented articular endoprostheses are generally made of titanium alloys and usually have a roughened (often sand-blasted) or textured porous surface in order to improve the integration of the bone tissue.

The prior art includes attempts aiming to improve the compatibility of the implant surfaces with respect to the bone tissue. Invariably, a load-bearing bulk phase is to contribute most of the requisite biomechanical properties (structural compatibility) and the surface phase is to ensure the compatibility (surface compatibility) to the adjoining bone tissue (WINTERMANTEL: Biokompatible Werkstoffe und Bauweisen: Implantate für die Medizin und Umwelt. Springer Verlag, Berlin, Heidelberg, New York, 1996). The underlying concept was to generate surface textures which would simulate the mineral phase of bone tissue. The mineral phase of human bone tissue is formed by a carbonate-apatite/hydroxyapatite. For this reason, the emphasis was on the development of calcium phosphate layers to improve the surface compatibility of implants.

Various methods (thermal spraying methods, electro-chemical deposition, sol-gel technologies, ion beam sputtering, laser ablation) have been used in regions contacting the bone tissue (articular endoprostheses of hip, knee, shoulder) attempting to improve the surface compatibility. Thus far, only plasma spraying (DE GROOT, KLEIN, WOLKE: Plasma-sprayed coatings of calcium phosphate. CRC Press, Boca Raton, Ann Arbor, Boston, 1990; DE GROOT, KLEIN, WOLKE: Chemistry of calcium phosphate bioceramics. CRC Handbook of bioactive ceramics, 2 (1996) 3-16: WO2009062671) and electrochemical deposition of calcium phosphate layers (BAN, MARUNO: Morphology and microstructure of electrochemically deposited calcium phosphates in a modified simulated body fluid. Biomaterials, 19 (1998) 1245-1253; DE4431862; WO2009147045; CN101485901; CN101406711; EP2037980; US2006134160; WO2004098436; WO2004024201; EP1264606; EP0774982; EP0232791) have become established on an industrial scale.

However, clinical long-term studies showed that plasma-sprayed calcium phosphate layers, initially considered to be stable in the long term, are subject to partial degradation in their bio-logical environment (WHEELER: Eight-year clinical retrospective study of titanium plasma-sprayed and hydroxyapatite-coated cylinder implants. International Journal of Oral and Maxillofacial Implants, 11,3 (1996) 340-350. OSHBORN: Die biologische Leistung der Hydroxylapatit-keramik-Beschichtung auf dem Femurschaft einer Titanendoprothese-erste histologische Auswertung eines Humanexplantats. Biomedizinische Technik, 32 (1987) 177-183.). During this process, there are phase changes at the interface to the bone tissue and the process leads to encapsulation and/or flaking mainly of crystalline components of the layer (particles).

Studies by Cooley (COOLEY, VAN DELLEN, BURGESS, WINDELER: The advantages of coated titanium implants prepared by radiofrequency sputtering from hydroxyapatite. J. Prosthet. Dent., 67 (1992) 93-100.) and Maxian (MAXIAN, ZAWADSKI, DUNN: Effect of CaP coating resorption and surgical fit on the bone/implant interface. Journal of Biomedical Material Research, 28 (1994) 1311-1319.) demonstrated the high efficiency of fully degradable, bioactive layers that were applied to metallic base bodies by means of electrochemical procedures. From the analysis of animal experiments and clinical studies, it was concluded that safe osseointegration at the implant surface is evident despite the rapid and complete degradation of highly soluble calcium phosphate layers.

It can therefore be noted that the rapidly soluble calcium phosphate layers can afford good clinical outcomes. Obviously, improved compatibility of implant surfaces with respect to the bone tissue does not require a coating on the implant surfaces that is stable in the long term.

However, like with all electrochemical deposition procedures common thus far, it is disadvantageous that a substantial equipment and time effort is required in order to apply these calcium phosphate layers to these medical implants.

Accordingly, there is a need for a simple, inexpensive, and rapidly applicable method that allows the surfaces of medical implants to be provided with coatings that promote bone growth.

The invention was therefore based on the object to provide a method for coating of a medical implant that can be used to apply a calcium salt to the surface of a medical implant easily and without expensive coating equipment and little expenditure of time. Said method shall be usable, in particular, right before implantation in the surgical theatre. Moreover, said method is to enable the manufacture of a coating of non-cemented articular endoprostheses that is both bone growth-stimulating and has a hemostyptic effect.

Moreover, a device is to be provided that can be used to implement the method according to the invention.

The object of the invention is met by a method for coating of a medical implant, through (i) providing a medical implant that includes at least one surface to be coated;

(ii) providing a body that includes at least one calcium salt with a Mohs hardness of no more than 5.5 on at least one of its surfaces; and (iii) rubbing said body having the calcium salt-containing surface onto the at least one medical implant surface to be coated in order to coat said surface of the medical implant with the at least one calcium salt.

Said method can be implemented with a device for coating a medical implant that includes a hollow body and a body that is arranged in the hollow body such as to be mobile therein and can be moved out of the hollow body at least in part, and comprises a calcium salt with a Mohs hardness of no more than 5.5 and a pharmaceutical agent.

The invention is based on the insight that medical implants, in particular non-cemented articular endoprostheses, usually have a rough or textured surface in order to attain good integration of the bone tissue. It has surprisingly been found that medical implants can be coated easily with calcium salts with a Mohs hardness of no more than 5.5 by rubbing said calcium salts onto said surfaces of the medical implants. Rubbing causes the soft calcium salt to be abraded and stay behind in the rough or textured surface of the medical implant. Since a coating needs to be present on the implant surfaces only temporarily, as is evidenced by the results obtained with dissolving calcium phosphate layers, the use of degradable, soft coating materials is feasible.

The invention therefore enables the coating of a medical implant with at least one calcium salt by the user right before the implantation in the surgical theatre. Accordingly, the implementation of the coating method according to the invention does not require any logistic pre-requisites to be provided such that, for example, knee endoprostheses made of various materials from a range of shapes and by different manufacturers can be coated with at least one calcium salt without any further technical aids. Aside from the at least one calcium salt, the surface to be coated can also be coated with one or more other substance(s) using the method according to the invention.

Accordingly, the invention provides a method for coating of a medical implant. In particular, a method for manufacture of a bone growth-promoting coating on the surface of a medical implant is being provided. Said method also renders the manufacture of a coating with a hemostyptic effect on the surface of a medical implant feasible. The coating of the surface of a medical implant with a calcium salt with a Mohs hardness of no more than 5.5 is also an object of the present method.

According to the invention, said method is performed outside the human or animal organism.

For this purpose, firstly, a medical implant that includes at least one surface to be coated is provided.

In the scope of the invention, coating of a medical implant shall be understood to be the covering of at least a part of at least one surface of the implant. According to a preferred embodiment, coating of a medical implant is to be understood to mean coating of at least 30%, more preferably at least 40%, even more preferably at least 50%, particularly preferably at least 60%, and most preferably at least 70% of at least one surface of the implant.

According to the invention, the term, medical implant, shall be understood to mean materials and devices that are introduced into the inside of the body, at least in part, in the course of a surgical intervention. Said implants can contact the bone and other elements of the musculo-skeletal apparatus or be in contact with blood or connective tissue.

According to a preferred embodiment, the medical implant is an endoprosthesis. Endoprostheses shall be understood to be implants that remain permanently inside the body and replace a body part partly or fully.

According to a particularly preferred embodiment, the medical implant is an articular endoprosthesis. Knee endoprostheses and hip endoprostheses are exemplary endoprostheses. Preferably, said articular endoprostheses are non-cemented articular endoprostheses.

These medical implants can be made of a variety of materials. According to a preferred embodiment, the medical implant comprises, or essentially consists of, titanium or titanium alloys.

According to the invention, it can be preferred that at least one of the surfaces is rough. According to a preferred embodiment, at least one surface of the medical implant has a mean roughness $R_a$ of at least 0.5 µm, particularly preferably of at least 0.75 µm, and most preferably of at least 1.0 µm. The men roughness $R_a$ is the mean distance of a measuring point—on the surface—from the centre line. The centre line intersects the true profile within the reference path such that the sum of the profile deviations (relative to the centre line) is minimised. Accordingly, the mean roughness $R_a$ corresponds to the arithmetic mean of the deviation from the centre line. According to the invention, a profile-based method using a surface profiler is preferred for measurement of the roughness. The at least one surface with a mean roughness $R_a$ of at least 0.5 µm, particularly preferably of at least 0.75 µm, and even more particularly preferably at least 1.0 µm, preferably is the surface to be coated of the medical implant. Surprisingly, it has been evident that rough implant surfaces are particularly easy and stable to coat with calcium salts. This might be based on rubbing the body that contains the at least one calcium salt onto the rough surface of the medical implant generates abrasion that contains the calcium salt and is deposited between the recesses that define the profile of the surface of the medical implant.

Moreover, the Mohs hardness of the medical implant surface to be coated preferably is at least 3.5, more preferably at least 4.0, even more preferably at least 4.5, and particularly preferably at least 5. It has been evident that the abrasion of the calcium salt with a Mohs hardness of no more than 5.5 on the surface of the medical implant is the larger, the larger the Mohs hardness of the surface to be coated of the medical implant. According to a particularly preferred embodiment, the medical implant surface to be coated has a Mohs hardness that is larger than the Mohs hardness of the calcium salt. According to another particularly preferred embodiment, the medical implant surface to be coated has a Mohs hardness that is larger than the Mohs hardness of the surface of the body that includes the calcium salt.

According to the invention, a body is used for coating of the medical implant which body includes on at least one of its surfaces at least one calcium salt with a Mohs hardness of no more than 5.5, more preferably of no more than 5.0, even more preferably of no more than 4.5, particularly preferably of no more than 4.0, and most preferably of no more than 3.5.

According to the invention, the term, "body", shall be understood to mean a tangible item or an object that has a three-dimensional geometric shape that can be described by boundary surfaces, and a mass. In the scope of the invention, body shall be understood to be any item without limitation to its geometry. In particular, the body can be a cylinder. The terms, "item" or "object", can be used as synonyms for the term, "body". According to a preferred embodiment, the body can be grasped with at least three fingers of one hand. According to another preferred embodiment, the body has a volume of at least 50 mm$^3$, more preferably has a volume of at least 100 mm$^3$, even more preferably has a volume of at least 250 mm$^3$, particularly preferably has a volume of at least 330 mm$^3$, and most preferably has a volume of at least 15000 mm$^3$.

The body includes on at least one of its surfaces at least one calcium salt with a Mohs hardness of no more than 5.5, more preferably of no more than 5.0, even more preferably of no more than 4.5, particularly preferably of no more than 4.0, even more particularly preferably of no more than 3.5, and in particular of no more than 3.1. Preferably, all surfaces of the body include at least one calcium salt with a Mohs hardness of no more than 5.5, more preferably of no more than 5.0, even more preferably of no more than 4.5, particularly preferably of no more than 4.0, even more particularly preferably of no more than 3.5, and in particular of no more than 3.1. According to a preferred embodiment, not just at least one surface of the body includes a calcium salt with a Mohs hardness of no more than 5.5, more preferably of no more than 5.0, even more preferably of no more than 4.5, particularly preferably of no more than 4.0, even more particularly preferably of no more than 3.5, and in particular of no more than 3.1. In particular, it is preferred that the at least one calcium salt with a Mohs hardness of no more than 5.5, more preferably of no more than 5.0, even more preferably of no more than 4.5, particularly preferably of no more than 4.0, even more particularly preferably of no more than 3.5, and in particular of no more than 3.1, is homogeneously or heterogeneously distributed throughout the body.

Preferably, the calcium salt that is present on at least one surface of the body is biocompatible.

According to a preferred embodiment, at least one surface of the body, in particular the surface of the body that is rubbed onto the surface to be coated of the implant, has a Mobs hardness of no more than 5.5, more preferably of no more than 5.0, even more preferably of no more than 4.5, particularly preferably of no more than 4.0, even more particularly preferably of no more than 3.5, and in particular of no more than 3.1.

Moreover, the porosity of the body preferably is in the range from 0-70% by volume. According to the invention, porosity is understood to mean the ratio of void volume to total volume of the body.

According to an embodiment, it can be preferred that the porosity of the body is in the range from 0-15%, more preferably in the range from 0-10%, and particularly preferably in the range from 0-5%. In these cases, the body preferably contains, aside from the at least one calcium salt, further ingredients, in particular the ingredients listed in the following (e.g. at least one pharmaceutical agent). Therefore, provided the user considers the presence of these ingredients in the implant coating necessary, the surface of the medical implant can be coated directly by means of said body without the user having to add these ingredients to the body. The low porosity of said body has proven to be particularly suitable in order to generate extensive abrasion of the at least one calcium salt on the surface of the medical implant.

According to another embodiment, it can be preferred that the porosity of the body is in the range from 10-70%, more preferably in the range from 20-70%, and particularly preferably in the range from 30-70%. In these cases, according to the invention, further ingredients, in particular the ingredients listed in the following (e.g. at least one pharmaceutical agent) are added to the body right before application. Provided the user considers the presence of these ingredients in the implant coating necessary, these ingredients can be added to the body and remain in the body due to the specified porosity. It is feasible, for example, to soak the bodies, before application, with a solution that contains at least one further ingredient, e.g. a pharmaceutical agent. Due to the specified porosity, the body is capable of taking up said ingredient. This usually lowers the porosity of the body which renders the surface of the medical implant easy and safe to coat by means of said body. This embodiment therefore makes it possible to prepare the body for the manufacture of a coating that contains further ingredients which are adapted to the specific needs of the recipient of the implant.

According to another preferred embodiment, the body has a water fraction in the range of 0-70% by weight. The water fraction can be based, for example, on water enclosed in the body and/or on crystal water associated with the calcium salts.

In this context, it can be preferred, on the one hand, that the water content of the body is in the range from 0-20% by weight, more preferably in the range from 0-10% by weight, and particularly preferably in the range from 0-5% by weight. Said water content can be present, on the one hand, when the body already contains all desired ingredients and can be used right away for the manufacture of the coating of the medical implant (ready-for-use"). On the other hand, said water content may be present when the body does not yet contain all ingredients, but rather further ingredients are to be added to the body right before application. Due to the low water content in this case, the body is capable of taking up solutions of said further ingredients. Accordingly, bodies with said low water content can be prepared easily, for example through soaking with a solution of the at least one further ingredient, in order to obtain a body that can be used to generate an implant coating that is adapted to the specific needs of the recipient of the implant.

On the other hand, it can be preferred that the water fraction of the body is in the range from 20-70% by weight, more preferably in the range from 25-65% by weight, and particularly preferably in the range from 30-60% by weight. Said water fraction is reached, in particular, in cases in which further ingredients are added to the body right before application, e.g. through soaking with an aqueous solution of the at least one further ingredient, and the body is not dried subsequently.

According to yet another preferred embodiment, the solubility of the calcium salt in water at a temperature of 25° C. is at least 2 g/l, more preferably is at least 5 g/l, and even more preferably is at least 10 g/l. Calcium salts that have high solubility in water and release calcium are preferred according to the invention, since they, being blood coagulation factors IV, are a hemostyptic agent and activate the blood coagulation cascade after the implantation. Blood coagulation being triggered by substances that are present on the surface of medical implant leads to the formation of a fibrin layer right after the implantation, which favours the medical implant growing on to the bone.

According to the invention, it can be preferred that the calcium salts contained in the body are inorganic calcium salts. However, it is feasible just as well that that the body also contains organic calcium salts aside from the inorganic calcium salts.

Preferably, the calcium salt fraction in the body is at least 50%, by weight, more preferably at least 60% by weight, even more preferably at least 70% by weight, particularly preferably at least 75% by weight, even more particularly at least 80% by weight, and in particular at least 85% by weight, relative to the weight of the body. The body can contain, for example, 50-100% by weight, more preferably 60-100% by weight, even more preferably 70-100% by weight, particularly preferably 75-100% by weight, even more particularly preferably 80-100% by weight, and in particular 85-100% by weight calcium salts, relative to the weight of the body. Also, the body can contain, for example, 50-90% by weight, more preferably 50-85% by weight, even more preferably 55-85% by weight, particularly preferably 60-85% by weight, even more particularly preferably 65-85% by weight, and in particular 60-80% by weight calcium salts, relative to the weight of the body.

According to another preferred embodiment, the calcium salt is selected from the group consisting of calcium sulfates, calcium phosphates, calcium hydrogen phosphates, and calcium carbonate.

According to the invention, the term, calcium salts, shall be understood to include both crystal water-containing calcium salts and crystal water-free calcium salts. Accordingly, the calcium salt can be selected, for example, from the group consisting of crystal water-containing calcium sulfate and crystal water-free calcium sulfate. In this context, the crystal water-containing calcium sulfate is preferably selected from the group consisting of calcium sulfate dihydrate and calcium sulfate hemihydrate. In this context, calcium sulfate dihydrate has proven to be particularly advantageous since it is porous in its hardened state and thus can soak up water or aqueous solutions. This is an easy means of subsequently soaking the body thus formed with aqueous solutions of further ingredients, such as, for example, pharmaceutical agents.

According to a particularly preferred embodiment, the calcium salt is selected from the group consisting of crystal water-free calcium sulfate, calcium sulfate dihydrate, and calcium sulfate hemihydrate.

According to another particularly preferred embodiment, the calcium phosphate is selected from the group consisting of crystal water-free calcium phosphate, alpha-tricalcium phosphate (α-TCP), and beta-tricalcium phosphate (β-TCP).

According to yet another particularly preferred embodiment, the calcium hydrogenphosphate is selected from the group consisting of brushite and monetite.

Preferably, the body further contains a compound that is selected from the group consisting of fatty acids, fatty acid esters, fatty acid salts, polyethylene glycols with a molar mass of no more than 1.000 g/mol, and oligomeric lactic acid esters with a molar mass of less than 1,000 g/mol. According to a particularly preferred embodiment, said compound is a glycerol tri-fatty acid ester.

Said compounds can, for example, serve to bind further ingredients, in particular further pharmaceutical agents, to the body. Moreover, said compounds can serve as binding agents in the manufacture of the bodies.

According to a further embodiment, the body contains a pharmaceutical agent.

Said pharmaceutical agent can preferably be selected from the group consisting of antibiotics, antiseptic agents, antiphlogistic agents, steroids, hormones, growth factors, bisphosphonates, cytostatic agents, gene vectors, and plasmids. According to a particularly preferred embodiment, the at least one pharmaceutical agent is an antibiotic.

The at least one antibiotic is preferably selected from the groups of aminoglycoside antibiotics, glycopeptide antibiotics, lincosamide antibiotics, quinolone antibiotics, oxazolidinone antibiotics, gyrase inhibitors, carbapenemes, cyclic lipopeptides, glycylcyclines, and polypeptide antibiotics, According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, tinidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a particularly preferred embodiment, the at least one antiphlogistic agent is selected from the group consisting of acetyl-salicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somato-tropin, testosterone, and estrogen.

The at least one growth factor is preferably selected from the group consisting of fibroblast growth factor (FGF), transforming growth factor (TGF), platelet-derived growth factor (PDGF), epidermal growth factor (EGF), vascular endothelial growth factor (VEGF), insulin-like growth factors (IGF), hepatocyte growth factor (HGF), bone morphogenic protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

The gene vector can be a viral vector or a cosmid vector.

There is no specific limitation with regard to the fraction of the body accounted for by the pharmaceutical agent. The fraction can, for example, be in the range from 0.1-30% by weight, more preferably in the range from 0.5-20% by weight, and particularly preferably in the range from 1-15% by weight, relative to the total weight of the body.

The pharmaceutical agent can be present as a coating on the body or distributed homogeneously in the body.

Moreover, the body can contain at least one colourant. It is particularly preferred for the colourant to be a food colourant. According to a particularly preferred embodiment, the colourant is selected from the group consisting of E101, E104, E132, E141 (chlorophyllin), E142, riboflavin, and lissamine green. According to the invention, the term, colourants, shall also include colour varnishes, such as, for example, colour varnish green, a mixture of E104 and E132. The presence of the colourant allows the user of the body to easily recognise, which regions of the medical implant are already coated and which are not, while the coating method according to the invention is being implemented.

In the scope of the invention, it can be preferred that the body contains at least one salt selected from the group consisting of magnesium salts, strontium salts, and lithium salts. Strontium sulfate, for example, is a preferred salt. These salts allow improved osseointegration of the medical implants coated by means of said body, in particular of the articular endoprostheses, to be attained.

According to a preferred embodiment, the body contains 70-90% by weight calcium sulfate and 10-30% by weight calcium carbonate. In this context, the calcium sulfate preferably is calcium sulfate dihydrate.

According to another preferred embodiment, the body contains 40-90% by weight calcium sulfate, 0.1-40% by weight calcium carbonate, and 0.1-20% by weight strontium sulfate. In this context, it can be preferred that the calcium sulfate is calcium sulfate dihydrate.

According to another preferred embodiment, the body contains 20-90% by weight calcium sulfate, 0.1-40% by weight calcium carbonate, and 0.5-50% by weight of a pharmaceutical agent.

According to yet another preferred embodiment, the body contains 70-73% by weight calcium sulfate, 16-20% by weight calcium carbonate, 8-10% by weight glycerol tri-palmitate, and 1-2% by weight gentamicin sulfate. The calcium sulfate preferably is calcium sulfate dihydrate.

The body according to the invention can be manufactured by a variety of routes.

According to a preferred embodiment, the body is manufactured by compressing a powder. Said powder preferably includes the same components preferably at the same composition as described herein with regard to the body. The body can be formed from said powder by simple compression, preferably using eccentric presses. Varying the offset allows the porosity and the abrasion behaviour of the body to be controlled. The addition of binding agents, in particular glycerol tri-fatty acid esters, has proven to be particularly advantageous in this context.

According to another preferred embodiment, the body is manufactured by casting a self-hardening mixture. Said self-hardening mixture preferably contains at least one calcium salt, e.g. calcium sulfate hemihydrate, and water. Preferably, the body is manufactured directly in the hollow body described below by pouring-in the self-hardening mixture. According to said embodiment, water-soluble or -suspendable components, for example pharmaceutical agents, can be introduced easily into the self-hardening mixture. Said components are therefore encapsulated in the body while the mixture hardens. Preferably, the mixture hardens through the addition of water to the calcium salt contained in the mixture. If said calcium salt is, e.g., calcium sulfate hemihydrate, calcium sulfate dihydrate is formed upon the addition of water. This addition causes the mixture to harden due to the formation of interwoven crystal structures.

At least one surface of a medical implant can be coated using the body described herein. For this purpose, the body having the calcium salt-containing surface is rubbed onto the at least one medical implant surface to be coated in order to coat said surface of the medical implant with the at least one calcium salt.

Preferably, rubbing the body shall be understood to mean mechanically pressing the body against the medical implant surface to be coated and, at the same time, performing back-and-forth movements of the body along the surface to be coated of the medical implant. Rubbing leads to abrasion of the at least one calcium salt contained on the surface of the body on the surface to be coated of the medical implant. In addition, the other ingredients of the body that are optionally contained therein are also abraded on the surface to be coated of the medical implant. Surprisingly, it has been found that the material abraded from the body is attached sufficiently stable on the surface of the medical implant in order to ensure safe introduction of the medical implant into the body.

Accordingly, the scope of the invention includes the use of a body, which includes a calcium salt having a Mohs hardness of no more than 5.5 on at least one of its surfaces, for applying, by rubbing, a coating that contains at least said calcium salt to a medical implant.

According to a preferred embodiment, the body is part of a device, particularly preferably in the form of a pen, that can serve for coating a medical implant. Said device includes (i) a hollow body and (ii) a body that is arranged in the hollow body such as to be mobile therein and can be moved out of the hollow body at least in part and comprises a calcium salt with a Mohs hardness of no more than 5.5 and a pharmaceutical agent.

The body that is arranged in the device preferably is a body according to the description provided herein. According to the invention, said body includes a pharmaceutical agent. Preferably, the device takes the shape of a cylinder. Preferably, the term, cylinder, shall be understood to mean a spherical body bordered by two parallel level planes (base and cover surface) and a jacket or cylinder surface that is formed by parallel straight lines. This term also includes bodies, in which the base surfaces and/or the cover surfaces are not planar, but rather are rounded or extend to be pointed. The cylinder preferably has a diameter of 5-25 mm and more preferably has a diameter of 10-15 mm. Using cylindrical bodies with said diameters, it is feasible to access and coat even surface regions of medical implant that are difficult to access.

The device according to the invention contains a hollow body. In this context, hollow body shall be understood to mean a body that includes a hollow space. The hollow body is designed such that it can harbour the body according to the invention, at least in part.

The body is accommodated, at least in part, in the hollow body. The body is arranged in the hollow space of the hollow body in such a manner as to be mobile in the hollow body. Preferably, the body is mobile in the hollow body along the axis of the hollow body. Moreover, the body is arranged in the hollow body such that the body can be guided out of the hollow space, at least in part.

Preferably, means are attached on the hollow body, on the body or on the hollow body and the body to allow at least part of the body to be guided out of the hollow body by means of pushing or rotational motions.

According to a preferred embodiment, means that enable the body to be locked in place in a position with respect to the hollow body are attached on the hollow body, on the body or on the hollow body and the body.

Moreover, it can be preferred for the hollow body to contain means that enable the hollow body to be grasped easily by the user. Moreover, it can be preferred to have means present on the hollow body that prevent the hand of the user from slipping in the direction of the body.

Accordingly, it is preferred that at least two and preferably four fins are attached perpendicularly on the outside of the hollow body, whereby two fins each are situated on an axis with respect to each other that intersects the axis of the hollow body perpendicularly. Preferably, two opposite fins are attached right on the opening of the hollow body on which the cylinder exits from the hollow body in order to prevent the user from possibly touching the body by hand or with gloves when he/she pushing the cylinder out by hand. Accordingly, it is possible to effectively reduce the risk of contamination through this arrangement. The two other fins can serve to hold the hollow cylinder while the body is being pushed out.

According to a preferred embodiment, the device according to the invention includes a plunger. The purpose of the plunger is to guide the body according to the invention out of the hollow body. Accordingly, said plunger is arranged, at least in part, in the hollow body. Preferably, the part of the plunger that is arranged in the hollow body is arranged such that it can be shifted in the hollow body. In this context, it is preferred that the part of the plunger that is arranged in the hollow body can be shifted along the axis of the hollow cylinder. Moreover, the plunger is preferably connected to the hollow body. Said connection can either be a rigid or a detachable connection. The plunger can, for example, be connected to the hollow body in a positive fit- or non-positive fit-type manner. Moreover, according to a preferred embodiment, the sum of the length of the plunger and length of the hollow body is larger than the length of the hollow cylinder.

Moreover, one or more fastening pins can be arranged on the front face of the plunger. Said fastening pins can serve for fixation of the body on the plunger. Preferably, a handle is arranged on the opposite face of the plunger. Said handle can be grasped by the user in the course of the application of the device according to the invention and thus is situated in the palm of the operator when the hollow body is being pushed out. When the hollow body is pushed out, the fins of the device are grasped with at least two fingers and pushed against the handle that is situated in the palm. This allows the plunger to move forward in the direction of the opening of the hollow body.

According to another preferred embodiment, at least one snap-in mechanism for the body is arranged on the hollow body, on the plunger or on the hollow body and the plunger. Preferably, mobile snap-in fins are arranged on the hollow body as snap-in device for the body and point in the direction of the axis of the body while they are in their resting position. Said snap-in device prevents the plunger from falling out of the hollow body while the body is rubbed onto the surface of the medical implant.

Moreover, it can be preferred that teeth or circumferential fastening fins are arranged on the plunger as snap-in device and recesses are arranged in the hollow body or that fastening fins or recesses are arranged on the hollow body as snap-in device and recesses are arranged in the plunger.

The invention shall be illustrated through the examples presented in the following, though without limiting the scope of the invention.

Example 1

A mixture of 71.7% by weight calcium sulfate dihydrate, 17.9% by weight calcium carbonate, 8.8% by weight glycerol tri-palmitate, and 1.6% by weight gentamicin sulfate was compressed with an eccentric press to form a cylinder with a diameter of 22 mm and a height of 10 mm. The cylinder was rubbed onto both sides of a sand-blasted titanium disc with a diameter of 27 mm. During the rubbing, a dense, colourless layer was formed. The mass of the coating was 124.7 mg. The disc was stored in 5 ml 0.1 M phosphate buffer at 37° C. After one day, all of the buffer was removed and replaced by fresh buffer. The buffer was exchanged again on day two and day seven. The buffer solution removed on each occasion was tested for its gentamicin content using a TDX analyzer made by Abbott.

| Day | Gentamicin released per square-centimeter of the surface of the titanium disc [µg/cm$^2$] |
|---|---|
| 1 | 92 |
| 2 | 18 |
| 6 | 1 |

Example 2

A mixture of 61.7% by weight calcium sulfate dihydrate, 10.0% by weight strontium sulfate, 17.9% by weight calcium carbonate, 8.8% by weight glycerol tri-palmitate, and 1.6% by weight gentamicin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 111.2 mg.

Example 3

A mixture of 61.7% by weight calcium sulfate dihydrate, 10.0% by weight strontium sulfate, 17.9% by weight calcium carbonate, 8.8% by weight glycerol tri-palmitate, and 1.6% by weight gentamicin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 111.2 mg.

Example 4

A mixture of 71.7% by weight calcium sulfate dihydrate, 17.9% by weight calcium carbonate, 8.8% by weight glycerol tri-palmitate, and 1.6% by weight gentamicin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 112.1 mg.

Example 5

A mixture of 71.9% by weight calcium sulfate dihydrate, 17.9% by weight calcium carbonate, 8.8% by weight glycerol tri-palmitate, and 1.4% by weight amikacin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 110.4 mg.

Example 6

A mixture of 72.3% by weight calcium sulfate dihydrate, 17.9% by weight calcium carbonate, 8.8% by weight glycerol tri-palmitate, and 1.0% by weight vancomycin hydrochloride was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 117.1 mg.

Example 7

A mixture of 70.0% by weight calcium sulfate dihydrate, 18.6% by weight calcium carbonate, 10.0% by weight polyethylene glycol 1000, and 1.4% by weight amikacin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 110.4 mg.

Example 8

A mixture of 71.9% by weight calcium sulfate dihydrate, 17.9% by weight calcium carbonate, 8.8% by weight palmitic acid, and 1.4% by weight amikacin sulfate was compressed with an eccentric press to form a cylinder with a diameter of 15 mm and a height of 30 mm. The cylinder was rubbed onto both sides of a sand-blasted titanium disc with a diameter of 27 mm. During the rubbing, a dense, colourless layer was formed. The mass of the coating was 113.2 mg.

Example 9

A mixture of 60% by weight calcium sulfate hemihydrate, 10% by weight calcium carbonate, 1.6% by weight gentamicin sulfate, and 28.4% by weight was mixed thoroughly. This resulted in a colourless, spreadable mass that was filled into a silicone mould. The silicone mould had an internal cylinder-shaped hollow space with a diameter of 15 mm and a length of 40 mm. The mass hardened after approx. 15 minutes. Then the cylinder was taken out and dried. The dried cylinder was rubbed onto a sand-blasted titanium disc with a diameter of 27 mm. The mass of the coating formed was 128.2 mg.

The invention claimed is:

1. Device for coating a medical implant comprising a hollow body and a body that is arranged in the hollow body such as to be mobile therein and can be moved out of the hollow body at least in part, and is or has at least one surface that is formed of a composition that comprises at least one calcium salt with a Mohs hardness of no more than 5.5, and a pharmaceutical agent, wherein the porosity of the body is in the range from 10-70% by volume.

2. The device according to claim 1 wherein the medical implant is an articular endoprosthesis.

3. The device according to claim 1 wherein the medical implant surface to be coated has a mean roughness $R_a$ of at least 0.5 μm.

4. The device according to claim 1 wherein the medical implant consists essentially of titanium or a titanium alloy.

5. The device according to claim 1 wherein the body comprises a water fraction in the range of from 20-70% by weight.

6. The device according to claim 1 wherein the solubility of the at least one calcium salt in water at a temperature of 25° C. is at least 2 g/l.

7. The device according to claim 1 wherein the body contains 50-100% by weight calcium salts.

8. The device according to claim 1 wherein said at least one calcium salt is selected from the group consisting of calcium sulfates, calcium phosphates, calcium hydrogenphosphates, and calcium carbonate.

9. The device according to claim 1 wherein the at least one calcium salt is selected from the group consisting of calcium sulfate dihydrate and calcium sulfate hemihydrate.

10. The device according to claim 1 wherein the body contains a compound that is selected from the group consisting of fatty acids, fatty acid esters, fatty acid salts, polyethylene glycols with a molar mass of no more than 1,000 g/mol, and oligomeric lactic acid esters with a molar mass of less than 1,000 g/mol.

11. The device according to claim 1 wherein the body contains a salt selected from the group consisting of magnesium salts, strontium salts, and lithium salts.

12. The device according to claim 1 wherein the body contains 70-90% by weight calcium sulfate and 10-30% by weight calcium carbonate.

13. The device according to any claim 1 wherein the body contains 20-90% by weight calcium sulfate, 0.1-40% by weight calcium carbonate, and 0.5-50% by weight of the pharmaceutical agent.

* * * * *